(12) United States Patent
Duran et al.

(10) Patent No.: US 8,680,280 B2
(45) Date of Patent: Mar. 25, 2014

(54) PROCESS FOR THE MANUFACTURING OF CRR INHIBITORS

(71) Applicants: Adil Duran, Biberach an der Riss (DE); Rolf Schmid, Baltringen (DE)

(72) Inventors: Adil Duran, Biberach an der Riss (DE); Rolf Schmid, Baltringen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/851,547

(22) Filed: Mar. 27, 2013

(65) Prior Publication Data
US 2013/0261307 A1  Oct. 3, 2013

(30) Foreign Application Priority Data
Apr. 2, 2012 (EP) .................................... 12162852

(51) Int. Cl.
*A61K 31/445* (2006.01)
*C07D 211/68* (2006.01)

(52) U.S. Cl.
USPC .......................................... 546/194; 514/318

(58) Field of Classification Search
USPC .......................................... 546/194; 514/318
See application file for complete search history.

(56) References Cited

U.S. PATENT DOCUMENTS

| | | |
|---|---|---|
| 4,289,781 A | 9/1981 | Bengtsson et al. |
| 6,433,165 B1 | 8/2002 | Luly et al. |
| 6,476,054 B1 | 11/2002 | Caldwell et al. |
| 8,278,302 B2 | 10/2012 | Grundl et al. |
| 2005/0182095 A1 | 8/2005 | Ting et al. |
| 2009/0123375 A1 | 5/2009 | Ambati |
| 2010/0261687 A1 | 10/2010 | Grundl et al. |
| 2012/0264729 A1 | 10/2012 | Frank et al. |
| 2013/0023517 A1 | 1/2013 | Grundl et al. |
| 2013/0261153 A1 | 10/2013 | Nivens et al. |
| 2013/0261307 A1 | 10/2013 | Duran et al. |
| 2013/0266646 A1 | 10/2013 | Fetscher et al. |

FOREIGN PATENT DOCUMENTS

| | | |
|---|---|---|
| EP | 0468187 A2 | 1/1992 |
| JP | 2002501052 A | 1/2002 |
| JP | 2002501898 A | 1/2002 |
| JP | 2006137718 A | 6/2006 |
| WO | 2006083390 A2 | 8/2006 |
| WO | 2006091671 A1 | 8/2006 |
| WO | 2007116313 A2 | 10/2007 |
| WO | 2008092681 A1 | 8/2008 |
| WO | 2009145721 A1 | 12/2009 |
| WO | 2010115836 A1 | 10/2010 |
| WO | 2012045803 A1 | 4/2012 |

OTHER PUBLICATIONS

Abstract in English of JP2006137718, 2006.
Bachert, C. et al., "Pharmacological Management of Nasal Polyposis." Drugs, 2005, vol. 65, No. 11, pp. 1537-1552.
Blanchard, C. et al., "Eotaxin-3 and a Uniquely Conserved Gene-Expression Profile in Eosinophilic Esophagitis." The Journal of Clinical Investigation, 2006, vol. 116, No. 2, pp. 536-547.
International Search Report and Written Opinion for PCT/EP2013/056638 mailed Jun. 21, 2013.
Takeda, A. et al., "CCR3 is a Target for Age-Related Macular Degeneration Diagnosis and Therapy." Nature, 2009, vol. 460, No. 7252, pp. 225-230.
De Lucca et al., "Discovery and Structure-Activity Relationship of N-(Ureidoalkyl)-Benzyl-Piperidines as Potent Small Molecule CC Chemokine Receptor-3 (CCR3) Antagonists". Journal of Medicinal Chemistry, vol. 45, 2002, pp. 3794-3804.
Sato et al., "Synthesis and structure-activity relations of N-{1-[(6-fluoro-2-naphthyl)methyl]piperidin-4-yl}benzamide derivatives as novel CCR3 antagonists". Bioorganic & Medicinal Chemistry, vol. 16, 2008, pp. 144-156.
Ting et al., "The synthesis of substituted bipiperidine amide compounds as CCR3 antagonists". Bioorganic & Medicinal Chemistry Letters, No. 15, 2005, pp. 1375-1378.
Wuts et al., "Protection for the Carboxyl Group". Greene's Protective Groups in Organic Synthesis, Ch. 5, 4th Edition, NY Wiley, 2007, pp. 553-559 and pp. 582-588.

*Primary Examiner* — John Mabry
(74) *Attorney, Agent, or Firm* — Michael P. Morris; Mary-Ellen M. Devlin

(57) ABSTRACT

The present invention relates to a process for preparing CCR3 inhibitors of formula 1,

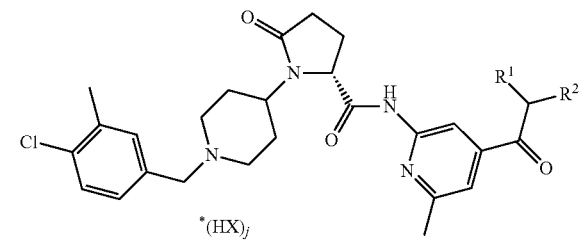

wherein
$R^1$ is H, $C_{1-6}$-alkyl, $C_{0-4}$-alkyl-$C_{3-6}$-cycloalkyl, $C_{1-6}$-haloalkyl;
$R^2$ is H, $C_{1-6}$-alkyl;
X is an anion selected from the group consisting of chloride or ½ dibenzoyltartrate
j is 1 or 2.

14 Claims, No Drawings

PROCESS FOR THE MANUFACTURING OF CRR INHIBITORS

The present invention relates to a process for preparing CCR3 inhibitors of formula 1,

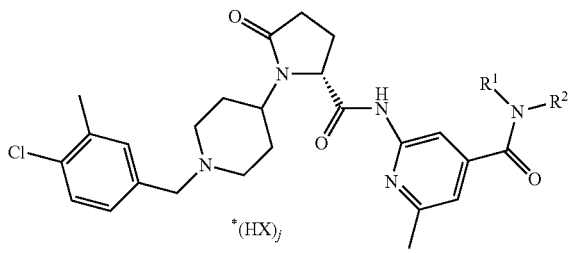

1 wherein
R$^1$ is H, C$_{1-6}$-alkyl, C$_{0-4}$-alkyl-C$_{3-6}$-cycloalkyl, C$_{1-6}$-haloalkyl;
R$^2$ is H, C$_{1-6}$-alkyl;
X is an anion selected from the group consisting of chloride or ½ dibenzoyltartrate
j is 1 or 2.

BACKGROUND INFORMATION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in Luster, New Eng. J Med., 338, 436-445 (1998); Rollins, Blood, 90, 909-928 (1997); Lloyd, Curr. Opin. Pharmacol., 3, 443-448 (2003); Murray, Current Drug Targets., 7, 579-588 (2006); Smit, Eur J Pharmacol., 533,277-88 (2006)

There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP2) and melanoma growth stimulatory activity protein (MGSA) are chemotactic primarily for neutrophils and T lymphocytes, whereas the CC chemokines, such as RANTES, MIP-1a, MIP-1, the monocyte chemotactic proteins (MCP-1, MCP-2, MCP-3, MCP-4, and MCP-5) and the eotaxins (-1, -2, and -3) are chemotactic for, among other cell types, macrophages, T lymphocytes, eosinophils, mast cells, dendritic cells, and basophils. Also in existence are the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seventransmembrane-domain proteins (reviewed in Horuk, Trends Pharm. Sci., 15, 159-165 (1994); Murphy, Pharmacol Rev., 54 (2):227-229 (2002); Allen, Annu. Rev. Immunol., 25, 787-820 (2007)) which are termed "chemokine receptors." On binding their cognate ligands, chemokine receptors transduce an intracellular signal through the associated trimeric G proteins, resulting in, among other responses, a rapid increase in intracellular calcium concentration, activation of G-proteins, changes in cell shape, increased expression of cellular adhesion molecules, degranulation, promotion of cell migration, survival and proliferation. There are at least eleven human chemokine receptors that bind or respond to CC chemokines with the following characteristic patterns: CCR-1 (or "CKR-1" or "CC-CKR-1") [MIP-1a, MCP-3, MCP-4, RANTES] (Ben-Barruch, et al., Cell, 72, 415-425 (1993), Luster, New Eng. J. Med., 338, 436-445 (1998)); CCR-2A and CCR-2B (or "CKR-2A"/"CKR-2B" or "CC-CKR-2A"/"CC-CKR-2B") [MCP-1, MCP2, MCP-3, MCP-4, MCP-5] (Charo et al., Proc. Natl. Acad. Sci. USA, 91, 2752-2756 (1994), Luster, New Eng. J. Med., 338, 436-445 (1998)); CCR3 (or "CKR-3" or "CC-CKR-3") [eotaxin-1, eotaxin-2, RANTES, MCP-3, MCP-4] (Combadiere, et al., J. Biol. Chem., 270, 16491-16494 (1995), Luster, New Eng. J. Med., 338, 436-445 (1998)); CCR-4 (or "CKR-4" or "CC-CKR-4") [TARC, MIP-1a, RANTES, MCP-1] (Power et al., J. Biol. Chem., 270, 19495-19500 (1995), Luster, New Eng. J. Med., 338, 436-445 (1998)); CCR-5 (or "CKR-5" OR"CCCKR-5") [MIP-1a, RANTES, MIP-1p] (Sanson, et al., Biochemistry, 35, 3362-3367 (1996)); CCR-6 (or "CKR-6" or "CC-CKR-6") [LARC] (Baba et al., J. Biol. Chem., 272, 14893-14898 (1997)); CCR-7 (or "CKR-7" or "CC-CKR-7") [ELC] (Yoshie et al., J. Leukoc. Biol. 62, 634-644 (1997)); CCR-8 (or "CKR-8" or "CC-CKR-8") [1-309, TARC, MIP-1p] (Napolitano et al., J. Immunol., 157, 2759-2763 (1996), Bernardini et al., Eur. J. Immunol., 28, 582-588 (1998)); CCR-10 (or "CKR-10" or "CC-CKR-10") [MCP-1, MCP-3] (Bonini et al, DNA and Cell Biol., 16, 1249-1256 (1997)); and CCR31 (or "CKR-11" or "CC-CKR-11") [MCP-1, MCP-2, MCP-4] (Schweickart et al., J Biol Chem, 275 9550-9556 (2000)).

In addition to the mammalian chemokine receptors, the Decoy receptors CCX-CKR, D6 and DARC/Duffy as well proteins expressed by mammalian cytomegaloviruses, herpes viruses and poxviruses, exhibit binding properties of chemokine receptors (reviewed by Wells and Schwartz, Curr. Opin. Biotech., 8, 741-748 (1997); Comerford, Bioessays., 29(3):237-47 (2007)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR-4, CCR2, CCR3, CCR5 and CCR8, can act as co receptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis, Grave's disease, chronic obstructive pulmonary disease, and atherosclerosis. For example, the chemokine receptor CCR3 is expressed among others on eosinophils, basophils, TH2 cells, alveolar macrophages, mast cells, epithelial cells, microglia cells, astrocytes and fibroblasts. CCR3 plays a pivotal role in attracting eosinophils to sites of allergic inflammation and in subsequently activating these cells. The chemokine ligands for CCR3 induce a rapid increase in intracellular calcium concentration, increased GTP exchange of G-proteins, increased ERK phosphorylation, enhanced receptor internalization, eosinophil shape change, increased expression of cellular adhesion molecules, cellular degranulation, and the promotion of migration. Accordingly, agents that inhibit chemokine receptors would be useful in such disorders and diseases. In addition, agents that inhibit chemokine receptors would also be useful in infectious diseases such as by blocking infection of CCR3 expressing cells by HIV or in preventing the manipulation of immune cellular responses by viruses such as cytomegaloviruses.

Therefore, CCR3 is an important target and antagonism of CCR3 is likely to be effective in the treatment of inflammatory, eosinophilic, immunoregulatory and infectious disorders and diseases (Wegmann, Am J Respir Cell Mol Biol., 36(1):61-67 (2007); Fryer J Clin Invest., 116(1):228-236 (2006); De Lucca, Curr Opin Drug Discov Devel., 9(4):516-524 (2006)

It has been found and disclosed in WO 2010 115836 that the substituted piperidines of formula 1 are highly suitable as CCR3 antagonists, having less side effects, e.g. inhibition of norepinephrine (NET), dopamine (DAT) or serotonin reuptake transporters (5-HTT) as described by Watson P S, Bioorg Med Chem Lett., 16(21):5695-5699 (2006), or inhibition of 5HT2A, 5HT2C or Dopamine D2 receptors as described by De Lucca, J Med Chem., 48(6):2194-2211 (2005), or inhibition of the hERG channel as described by De Lucca, Curr Opin Drug Discov Devel., 9(4):516-524 (2006), or inhibition of the alpha1B adrenergic receptor.

Nevertheless the synthesis of these compounds was complicated, needed a lot of several steps and was very time consuming. Thus, the goal of the present invention is to provide a clean and fast way to synthesize compounds of formula 1 starting from commercially available educts.

Basis is a Lewis acid induced aminolyse which is also known from Mark W. Bundesmann et al. Tetrahedron Letters 51; 3879-3882; 2010. Nevertheless prior art does not cite that this reaction is also with optionally substituted pyridines like compound 2 (see below) possible.

DESCRIPTION OF THE INVENTION

The present invention relates to a process for preparing compounds of formula 1,

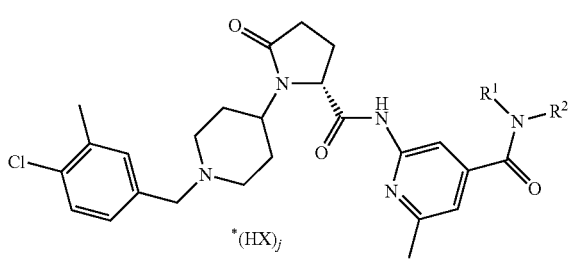

1 characterised in that a) a compound of formula 2

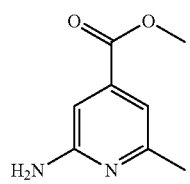

2 is reacted with $NHR^1R^2$ (3) to a compound of formula 4

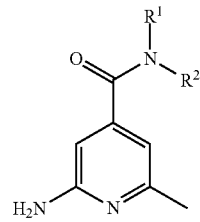

4 and thereafter is b) coupled with a compound of formula 5,

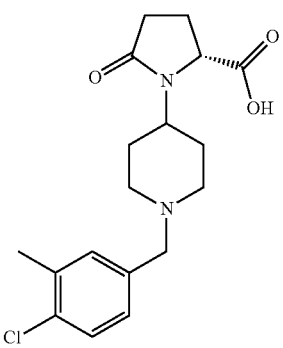

5 wherein for the formula 1, 3 and 4, dependent from each other
$R^1$ is H, $C_{1-6}$-alkyl, $C_{0-4}$-alkyl-$C_{3-6}$-cycloalkyl, $C_{1-6}$-haloalkyl;
$R^2$ is H, $C_{1-6}$-alkyl;
X is an anion selected from the group consisting of chloride or ½ dibenzoyltartrate,
j is 1 or 2.
 Preferred is a process wherein
$R^1$ is H, $C_{1-6}$-alkyl;
$R^2$ is H, $C_{1-6}$-alkyl;
X is an anion selected from the group consisting of chloride or ½ dibenzoyltartrate
j is 1 or 2.
 Preferred is a process wherein
$R^1$ is H, Methyl, Ethyl, Propyl, Butyl;
$R^2$ is H, Methyl, Ethyl, Propyl, Butyl;
X is an anion selected from the group consisting of chloride or ½ dibenzoyltartrate, preferably chloride;
j is 1 or 2, preferably 2.
 Preferred is a process wherein
$R^1$ is H, Methyl, Ethyl, Propyl, Butyl;
$R^2$ is H, Methyl;
X is an anion selected from the group consisting of chloride or ½ dibenzoyltartrate, preferably chloride;
j is 1 or 2, preferably 2.
 Preferred is a process wherein
$R^1$ is H, Methyl;
$R^2$ is H, Methyl;
X is an anion selected from the group consisting of chloride or ½ dibenzoyltartrate, preferably chloride;
j is 1 or 2, preferably 2.
 Preferred is a process wherein X is chloride.
 Preferred is a process wherein j is 2.
 Preferred is a process wherein compound 2 is reacted with a compound of formula 3 in a solvent selected from the group consisting of methanol, ethanol, isopropanol, t-amylalkohol, t-butanol, tetrahydrofuran, 2-methyl tetrahydrfuran, acetonitril, 1,4-dioxan, N-methyl pyrrolidone and N,N'-dimethylformamide, preferred is methanol or ethanol.

Preferred is a process wherein compound 2 is reacted with 3 in the presence of a Lewis acid selected from the group consisting of magnesium methoxide, magnesium chloride, calcium chloride and zinc chloride; preferred is magnesium methoxide.

Preferred is a process wherein compound 3 is added to the compound 2 at a temperature below 20° C., preferably, 15°, preferably 10° C., preferably about 5° C., preferably 0° C., preferably −5° C., preferably −7° C. and preferably −10° C., preferable 10 to −10° C.

Preferred is a process wherein the reaction mixture of compound 2 and 3 is heated after adding of 2 and 3 for more than 4 h, preferably 6 h, preferably 7 h, preferably 15 h, preferably 24 h.

Preferred is a process wherein the reaction mixture of compound 2 and 3 is heated after adding of 2 and 3 for 4 h to 10 h, preferably 6 to 10 h, preferably 7 h to 9 h, preferably 15 to 24, most preferred about 8 h.

Preferred is a process wherein the reaction mixture of compound 2 and 3 is heated above 50° C., preferably, 60° C., preferably 70° C., preferably 80 to 100° C.

Preferred is a process wherein compound 4 is reacted with a compound of formula 5 in a solvent selected from the group consisting of toluene, o-, m-. p-xylene, tetrahydrofuran, 2-methyl tetrahydrofuran, N-methyl pyrrolidone, acetonitrile, and 1,4-dioxane, preferably toluene.

Preferred is a process wherein compound 4 is reacted with a compound of formula 5 in the presence of a base selected from the group consisting of triethylamine, diisopropyl ethylamine and 4-methylmorpholine, preferably triethylamine.

Preferred is a process wherein the reaction mixture of compound 4 and 5 is heated above 50° C., preferably, 60° C., preferably 70° C., preferably 80° C., preferably 70 to 90° C.

Preferred is a process wherein to the reaction mixture of compound 4 and 5 a compound selected from the group consisting of 1-propylphosphonic acid cyclic anhydride 50% solution (T3P), N,N'-carbonyldiimidazol (CDI), N,N'-dicyclohexylcarbodiimid (DCC) and N,N'-diisopropylcarbodiimid (DIC), preferably T3P is added.

Preferred is a process wherein the reaction mixture of compound 4 and 5 is heated for more than 1 h, preferably 2 h, preferably 3 h, preferably 4 to 8 h.

Preferred is a process wherein the product 1 is obtained by precipitation form a hydrochloric acid containing solvent selected from ethanol and acetone.

Preferred is a process wherein the compound of formula 5 is c) made by reductive amination of a compound of formula 9 or a salt thereof, if a salt preferably the hydrochloride

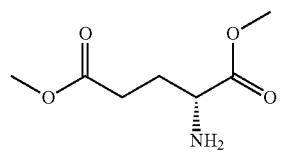

with a compound of formula 8

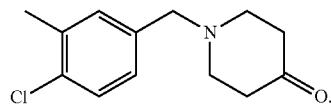

and d) adding of hydrogen.

Preferred is a process wherein compound 8 is reacted with a commercially available compound of formula 9 or a salt thereof in a solvent selected from the group consisting of methanol, ethanol, isopropanol, t-amylalkohol, t-butanol, tetrahydrofuran, 2-methyl tetrahydrfuran, acetonitril, 1,4-dioxan, N-methyl pyrrolidone and N,N'-dimethylformamide, preferably ethanol.

Preferred is a process wherein compound 8 is reacted with 9 or a salt thereof in the presence of a base selected from sodium methylate, sodium carbonate, potassium carbonate and sodium hydroxide, preferably sodium carbonate.

Preferred is a process wherein the reaction mixture of compound 8 and 9 or a salt thereof is stirred after adding of the base from 5 to 500 min, preferably 10 to 400 min, preferably 10 to 275 min, preferably 10 to 150 min, preferably 10 to 60 min.

Preferably the reductive amination step c) for producing compound 10 is carried out d) with following addition of hydrogen in the presence of a heavy metal catalyst, preferably a platinum catalyst and contains no risk for racemisation.

Preferred is a process wherein a platinum catalyst, preferably a platinum (IV) oxide, a platinum on activated carbon, a palladium on activated carbon or a Raney-nickel catalyst, preferably platinum(IV)oxide is added for hydrogenation in the presence of hydrogen.

Preferred is a process wherein the hydrogenation takes place at hydrogen pressure above 1 bar, preferably between 1 to 100 bar, preferably 1 to 10 bar, most preferably 3 to 10 bar Preferred is a process wherein the hydrogenation takes at least 1 hour, preferably more than 1 hour, preferably 2 to 4 hours at room temperature and thereafter is heated for at least 1 hour, preferably more than 1 hour, preferably 2 to 5 hours, preferably 6 to 8 h.

Preferred is a process wherein after the hydrogenation the catalyst is removed by filtration.

Preferred is a process wherein the compound of formula 8 is made by reacting a compound of formula 6,

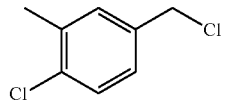

with a compound of formula 7

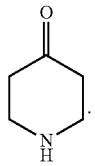

Preferred is a process wherein compound 6 is reacted with a compound of formula 7 in a solvent selected from the group consisting of tetrahydrofuran (THF), 2-methyl tetrahydrofuran, N,N'-dimethylformamide (DMF), N-methyl pyrrolidone, acetonitrile, 1,4-dioxane, and mixtures thereof.

Preferred is a process wherein compound 6 is reacted with 7 in the presence of potassium carbonate, sodium carbonate and sodium hydroxide, preferably potassium carbonate Preferred is a process wherein the reaction mixture of compound 6 and 7 is heated after adding for more than 4 h, preferably 6 h, preferably about 7 h. Preferred is a process wherein the reaction mixture of compound 6 and 7 is heated above 50° C., preferably, 60° C., preferably 70° C., preferred about 80° C.

Used Terms and Definitions

The term "about" means 5% more or less of the specified value. Thus, about 100 minutes could also be read as from 95 to 105 minutes.

If a range is defined the upper and lower end of the range is per definition included, i.e. a range between 10 to 20° C. includes 10° C., 20° C. and every temperature between.

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general, for groups comprising two or more subgroups, the first named subgroup is the radical attachment point, for example, the substituent "$C_{1-3}$-alkyl-aryl" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk is may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-haloalkyl", wherein n is an integer from 2 to n, either alone or in combination with another radical denotes an acyclic, saturated, branched or linear hydrocarbon radical with 1 to n C atoms wherein one or more hydrogen atoms are replaced by a halogene atom selected from among fluorine, chlorine or bromine, preferably fluorine and chlorine, particularly preferably fluorine. Examples include: $CH_2F$, $CHF_2$, $CF_3$.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

Preparation

The one arm of the synthesis pathway is the reaction of the commercially available compound 2 to a compound of 4 whereas only one reaction step is needed to result the product in high yield and purity and a following reaction with compound 5 (see below) to the final product 1.

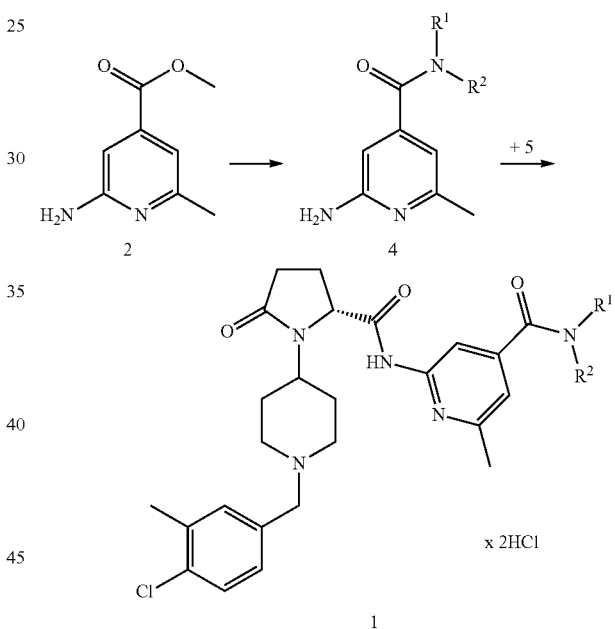

Synthesis of compound 4: (the following synthesis is exemplified for $R^1$ and $R^2$ being methyl, nevertheless the synthesis works also if $R^1$ is H, $C_{1-6}$-alkyl, $C_{0-4}$-alkyl-$C_{3-6}$-cycloalkyl, $C_{1-6}$-haloalkyl; and $R^2$ is H, $C_{1-6}$-alkyl). Method A: A mixture of 2-Amino-6-methyl-isonicotinic acid methyl ester (2, 10.00 kg; 60.18 mol) and magnesium methoxide 7% w/w solution in methanol (111.39 kg; 90.26 mol) were cooled down to 5° C. and dimethyl amine gas (3', 27.13 kg; 601.76 mol) was condensed into the reaction mixture. The vessel was sealed and heated at 80° C. for 8 h. Afterwards, The mixture was cooled to 20° C. and Celite (10.0 kg) was added to the obtained suspension. The solid was collected by filtration and washed with 20.0 L methanol. The filtrate was transferred to a second vessel, first 100 L solvent was removed via distillation at atmospheric pressure and further 45.0 L solvent was removed via vacuum distillation. 80.0 L toluene was added and 70.0 L solvent was removed again via vacuum distillation. 65.0 L toluene was added and the mixture was stirred at 20° C. for ½ h. The solid was collected by centrifugation, washed with 30.0 L toluene and dried under vacuum at 60° C. to obtain compound 4 as an off-white solid (10.46 kg), overall yield 97% theoretical. $^1$H NMR (400 MHz, DMSO-d$_6$) δ 6.27 (s, 1H), 6.14 (s, 1H), 5.97 (s, 2H), 2.93 (s, 3H), 2.86 (s, 3H), 2.24 (s, 3H); HPLC purity typically above 96% a/a. Method B: A mixture of 2-Amino-6-methyl-isonicotinic acid methyl ester (2, 10.00 g; 60.18 mmol), magnesium methoxide (solid) (8.9 g; 103.15 mmol) and methanol (130 ml) were cooled down to −7° C. and dimethyl amine gas (3', 27.13 g; 601.77 mmol) was condensed into the reaction mixture. The reaction tube was sealed and heated at 80° C. for 8 h. Further procedure and work up was according to the above description in method A. The obtained yield and purity was comparable to method A.

Synthesis of compound 1: A mixture of compound 5 (10.00 kg; 28.50 mol), compound 4 (6.64 kg; 37.05 mol), toluene (80.0 L) and triethylamine (10.09 kg; 99.76 mol) were heated (internal temperature 77° C.). 1-propylphosphonic acid cyclic anhydride 50% w/w in THF (36.25 kg; 57.00 mol) was slowly added in about 0.5 h. The mixture was than stirred for 3.0 h. After this time the reaction mixture was cooled (internal temperature 25° C.) and purified water (58.5 L) was added. The pH of the mixture was adjusted to 9 by adding sodium hydroxide 50% w/w (4.56 kg; 57.00 mol) and then the phases were separated. The organic layer was concentrated under vacuum (~80.0 L) and acetone (80.0 L) was added. The mixture was filtered to a second vessel, rinsed with acetone (15.0 L) and hydrochloric acid in ethanol (10 N; 5.41 kg; 58.43 mol) was added at 50° C. Ethanol (3.0 L) and acetone (25.0 L) were used to wash the line. A thick suspension was obtained and the stirring was continued for 2.0 h (internal temperature 58° C.). The slurry was cooled to 5° C. within 3.0 h and the stirring was continued for further 0.5 h. The solid was collected by filtration, washed with acetone (2×30.0 L) and dried under vacuum at 70° C. for about 15 h to obtain compound 1 (13.81 kg) as white crystals, overall yield 83% theoretical. $^1$H NMR (400 MHz, DMSO-d$_6$) δ 11.00 (s, 1H), 10.50 (bs, 1H), 7.82 (s, 1H), 7.53 (s, 1H), 7.47 (d, 1H), 7.39 (d, 1H), 6.99 (s, 1H), 4.52 (d, 1H), 4.17 (d, 2H), 3.97-3.84 (m, 1H), 3.39-3.24 (m, 2H), 3.09-2.90 (m, 2H), 2.98 (s, 3H), 2.86 (s, 3H), 2.45 (s, 3H), 2.32 (s, 3H), 2.38-2.04 (m, 4H), 2.04-1.65 (m, 4H)

In a preferred embodiment of the above process the compound of formula 5 is made starting from the commercially available compound 6.

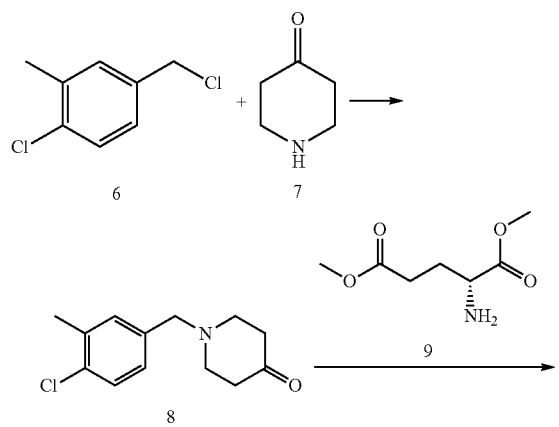

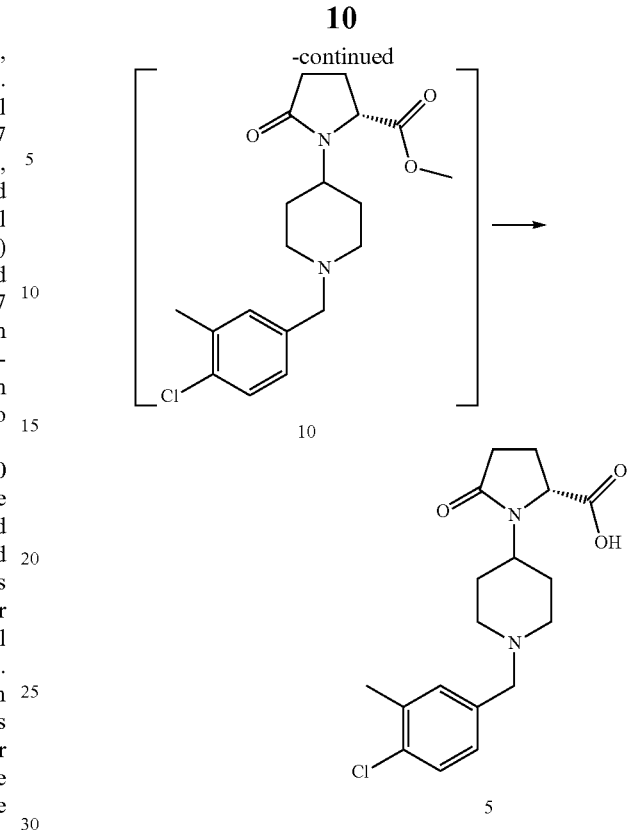

Synthesis of compound 8: 1-Chloro-4-(chloromethyl)-2-methylbenzene (6, 16.70 kg; 95.40 mol) and 4-piperidone hydrochloride hydrate (7, 16.12 kg; 104.94 mol) were mixed in THF (50.1 L) and DMF (8.4 L). The reaction mixture was heated (internal temperature 50° C.) and a solution of potassium carbonate (27.69 kg; 200.33 mol) in purified water (55.1 L) was added. The obtained slurry was heated for 7 h (internal temperature 70° C.). Afterwards, the mixture was cooled to 50° C. and more purified water (10.0 L) was added. The cooling was continued (internal temperature 25° C.) and then the phases were separated. The organic layer was concentrated via vacuum distillation as much as possible and the crude product was isolated as an oil (24.42 kg), overall yield >99%. The purity of the obtained crude material was sufficient and further purification was not necessary. $^1$H NMR (400 MHz, DMSO-d$_6$) δ 7.36 (d, 1H), 7.32 (s, 1H), 7.19 (s, 1H), 3.56 (s, 2H), 2.67 (t, 4H), 2.34 (t, 4H), 2.33 (s, 3H)

The reductive amination step for producing compound 10 is carried out by hydrogen and a platinum catalyst and contains no risk for racemisation.

Synthesis compound of 5: Compound 8 (16.00 kg; 67.30 mol), commercially available dimethyl D-glutamate hydrochloride (9, 17.81 kg; 84.13 mol) and ethanol (112. 0 L) were charged in a vessel. A sodium methylate 30% w/w solution in methanol (15.15 kg; 84.13 mol) was added by maintaining the internal temperature at 22° C. The line was washed with ethanol (16.0 L) and the reaction mixture was stirred for 15 min., afterwards, acidic acid (8.08 kg; 134.61 mol) was added and the line was washed with ethanol (10.0 L). A slurry of platinum catalyst (0.20 kg, platinum (IV) oxide) in ethanol (10.0 L) was added to the reaction mixture. The mixture was stirred with hydrogen pressure (3-4 bar; internal temperature 50° C.) 2-4 h. After this time, the internal temperature was increased to 80° C. and stirring was continued for further 4 h. Afterwards, the mixture was cooled (internal temperature 30° C.), purified water (64.0 L) was added and stirring was continued for further 10 min. The catalyst was filtered off and rinsed with ethanol (32.0 L). The filtrate was transferred to a second vessel, rinsed with ethanol (16.0 L) and concentrated via vacuum and isopropyl acetate (IPAc) (112.0 L) was added. The mixture was cooled (internal temperature 20° C.) and sodium hydroxide solution 50% w/w (11.85 kg; 148.07 mol) was added and the line was washed with purified water (16.0 L) and the phases were separated. The organic layer was concentrated via vacuum distillation and the remaining oil (which is non-purified compound 10) was solved in ethanol (64.0 L). Sodium hydroxide 50% w/w solution, purified water (3.2 L) and ethanol (40. L) were charged in a third vessel and heated (internal temperature 60° C.). The ethanolic solution of compound 10 was added to the third vessel in about 15 min. The line was washed with ethanol (16.0 L). Afterwards, the mixture was cooled (internal temperature 20° C.) and the pH was adjusted to about 7.5 by adding acetic acid (4.64 kg; 77.39 mol) and the line was rinsed with ethanol (8.0 L). The solution was cooled down (internal temperature −4° C.) and seeded (8.0 g of compound 5 available from previous processes or for the first time according to prior art i.e. WO 2010115836). Stirring was continued for 12 h (internal temperature −4° C.). The solid was collected by centrifugation, washed with cold ethanol (32 L) and dried under vacuum at 40° C. for about 15 h to obtain compound 5 (14.19 kg) as white crystals, overall yield 63% theoretical. $^1$H NMR (400 MHz, DMSO-$d_6$) δ 7.34 (d, 1H), 7.27 (s, 1H), 7.14 (d, 1H), 4.14 (d, 1H), 3.74-3.63 (m, 1H), 3.46 (d, 2H), 2.85 (d, 2H), 2.31 (s, 3H), 2.28-1.49 (m, 10H)

The following examples for the free base of a compound of formula 1 can be synthesized according to the description of WO 2010 115836, which is herewith incorporated by reference. The salts can be formed by crystallizing the free bases from a solution containing HCl or dibenzoyl tartaric acid.

| Example # | Structure |
|---|---|
| 1. | 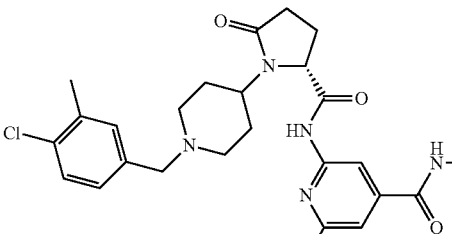 |
| 2. | 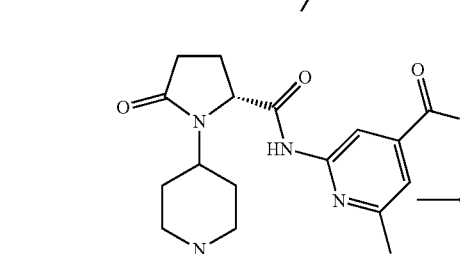 |
| 3. | 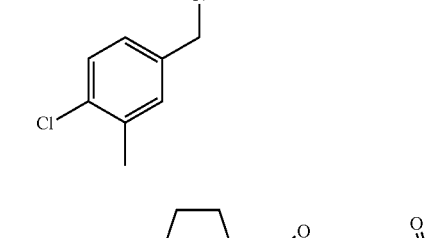 |
| 4. | 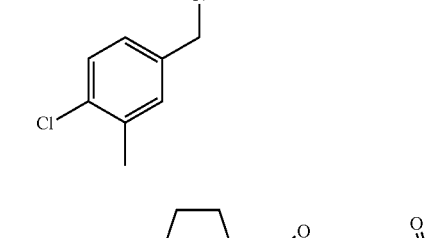 |
| 5. | 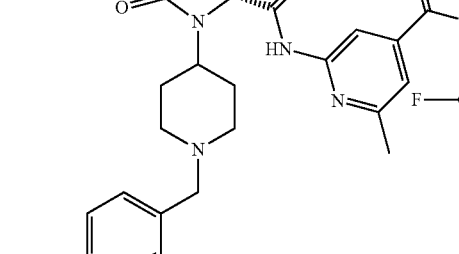 |
| 6. | 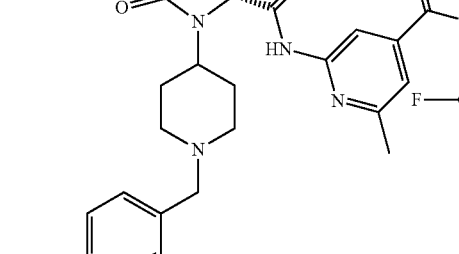 |

-continued

| Example # | Structure |
|---|---|
| 7. | 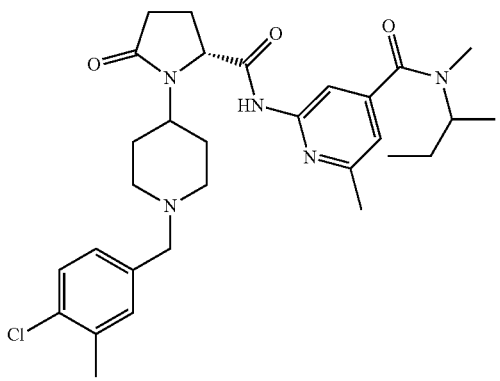 [SMILES: CCC(C)N(C)C(=O)c1cc(C)nc(NC(=O)[C@H]2CCC(=O)N2C2CCN(Cc3ccc(Cl)c(C)c3)CC2)c1] |
| 8. | 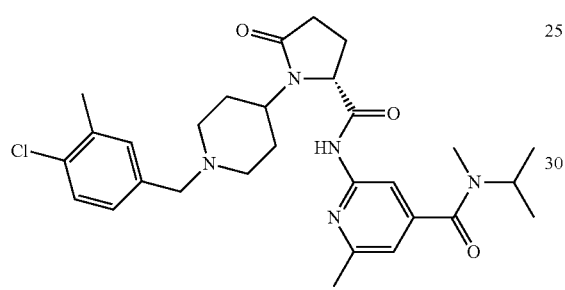 |
| 9. | 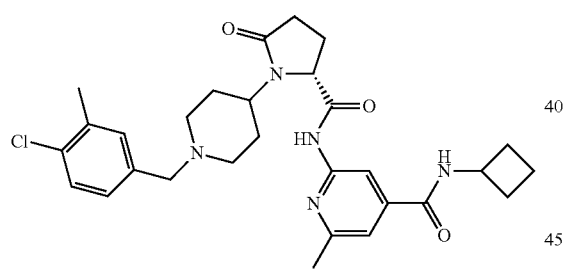 |
| 10. | 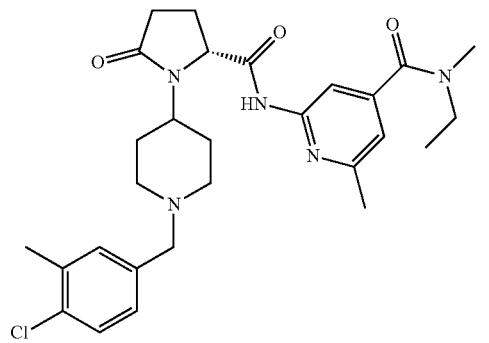 [SMILES: CCN(C)C(=O)c1cc(C)nc(NC(=O)[C@H]2CCC(=O)N2C2CCN(Cc3ccc(Cl)c(C)c3)CC2)c1] |

Preferably the above shown examples 1, 2 3, 4, 5, 6, 7, 8, 9 and 10 are in form of the hydrochloride.
Preferably the above shown examples 1, 2 3, 4, 5, 6, 7, 8, 9 and 10 are in form of the dihydrochloride.
Preferably the above shown examples 1, 2 3, 4, 5, 6, 7, 8, 9 and 10 are in form of the dibenzoyltartrate.

What is claimed is:

1. A process for preparing a compound of formula 1,

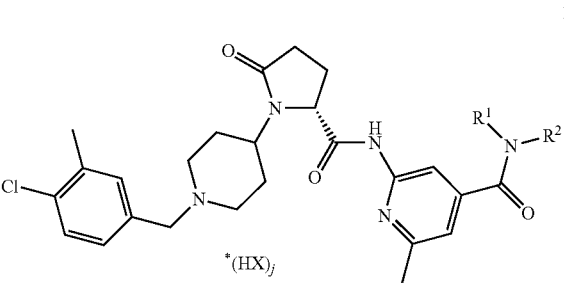

1 characterised in that a) a compound of formula 2

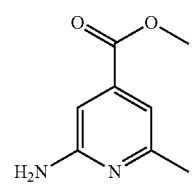

2 is reacted with $NHR^1R^2$ (3) to a compound of formula 4

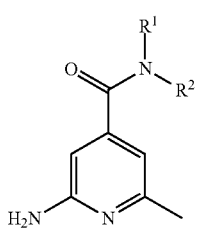

4 and b) thereafter is coupled with a compound of formula 5,

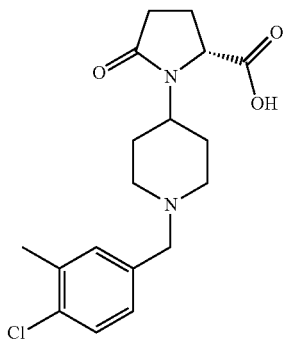

5 wherein for formulas 1, 3 and 4, dependent from each other
$R^1$ is H, $C_{1-6}$-alkyl, $C_{0-4}$-alkyl-$C_{3-6}$-cycloalkyl, $C_{1-6}$-haloalkyl;
$R^2$ is H, $C_{1-6}$-alkyl;
X is an anion selected from the group consisting of chloride or ½ dibenzoyltartrate
j is 1 or 2.

2. The process according to claim 1, wherein
R¹ is H, Methyl, Ethyl, Propyl, Butyl;
R² is H, Methyl, Ethyl, Propyl, Butyl;
X is an anion selected from the group consisting of chloride or ½ dibenzoyltartrate, preferably chloride;
j is 1 or 2, preferably 2.

3. The process according to claim 1, wherein X is chloride and j is 2.

4. The process according to claim 1, wherein step a) is conducted in a solvent selected from the group consisting of methanol, ethanol, isopropanol, t-amylalkohol, t-butanol, tetrahydrofuran, 2-methyl tetrahydrfuran, acetonitril, 1,4-dioxan, N-methyl pyrrolidone and N,N'-dimethylformamide.

5. The process according to claim 1, wherein step a) is conducted in the presence of a Lewis acid selected from the group consisting of magnesium methoxide, magnesium chloride, calcium chloride and zinc chloride.

6. The process according to claim 1, wherein step b) is conducted in a solvent selected from the group consisting of toluene, o-, m-, p-xylene, tetrahydrofuran, 2-methyl tetrahydrofuran, N-methyl pyrrolidone, acetonitrile, and 1,4-dioxane.

7. The process according to claim 1, wherein step b) is conducted in the presence of a base selected from the group consisting of triethylamine, diisopropyl ethylamine and 4-methylmorpholine.

8. The process according to claim 1, wherein step b) is conducted in the presence of 1-propylphosphonic acid cyclic anhydride 50% solution (T3P), N,N'-carbonyldiimidazol (CDI), N,N'-dicyclohexylcarbodiimid (DCC) or N,N'-diisopropylcarbodiimid (DIC).

9. The process according to claim 1, wherein 1 is obtained by precipitation form a hydrochloric acid containing solvent selected from ethanol and acetone.

10. The process according to claim 1, wherein c) the compound of formula 5 is made by reacting a compound of formula 9 or a salt thereof

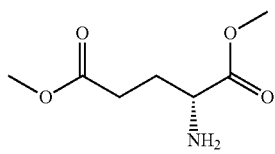

with a compound of formula 8

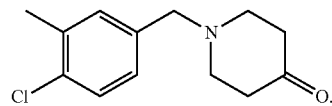

and d) adding of hydrogen.

11. The process according to claim 1, wherein step c) and d) is conducted in a solvent selected from the group consisting of methanol, ethanol, isopropanol, t-amylalkohol, t-butanol, tetrahydrofuran, 2-methyl tetrahydrfuran, acetonitril, 1,4-dioxan, N-methyl pyrrolidone and N,N' -dimethylformamide.

12. The process according to claim 1, wherein step c) and d) is conducted in the presence of a base selected from sodium methylate, sodium carbonate, potassium carbonate and sodium hydroxide.

13. The process according to claim 1, wherein between step c) and step d) the mixture is stirred between 5 and 500 min.

14. The process according to claim 1, wherein step d) is carried out at a hydrogen pressure between 1 to 100 bar in the presence of a heavy metal catalyst.

* * * * *